(12) United States Patent
Chimmalgi et al.

(10) Patent No.: US 9,110,037 B2
(45) Date of Patent: Aug. 18, 2015

(54) DIODE LASER BASED BROAD BAND LIGHT SOURCES FOR WAFER INSPECTION TOOLS

(71) Applicant: KLA-Tencor Corporation, Milpitas, CA (US)

(72) Inventors: Anant Chimmalgi, San Jose, CA (US); Younus Vora, San Jose, CA (US); Rudolf Brunner, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/521,977

(22) Filed: Oct. 23, 2014

(65) Prior Publication Data

US 2015/0042979 A1  Feb. 12, 2015

Related U.S. Application Data

(63) Continuation of application No. 13/924,216, filed on Jun. 21, 2013, now Pat. No. 8,896,827.

(60) Provisional application No. 61/664,493, filed on Jun. 26, 2012.

(51) Int. Cl.
*G01N 21/00* (2006.01)
*G01N 21/95* (2006.01)
(Continued)

(52) U.S. Cl.
CPC ........ *G01N 21/9501* (2013.01); *G01N 21/8806* (2013.01); *G03F 7/70483* (2013.01); *G01N 2021/8845* (2013.01); *G01N 2021/95676* (2013.01); *G01N 2201/0612* (2013.01)

(58) Field of Classification Search
CPC ........... G02B 19/0057; G02B 19/0014; G02B 19/0023; G02B 19/0028; G02B 19/0052; G02B 19/009; G02B 23/04; G02B 27/0905; G02B 27/0911; G02B 27/0961; G02B 27/0966; G02B 27/10; G02B 27/1006; G02B 27/14
See application file for complete search history.

(56) References Cited

U.S. PATENT DOCUMENTS 5,715,270 A  2/1998  Zediker et al.
6,104,481 A  8/2000  Sekine et al.
(Continued)

FOREIGN PATENT DOCUMENTS

KR  1020100134715 A  12/2010
WO  2008151266 A2  12/2008

OTHER PUBLICATIONS

"U.S. Appl. No. 13/924,216, Non Final Office Action mailed Mar. 17, 2014", 7 pgs.
(Continued)

*Primary Examiner* — Michael P Stafira
(74) *Attorney, Agent, or Firm* — Kwan & Olynick LLP

(57) ABSTRACT

Disclosed are methods and apparatus for performing inspection or metrology of a semiconductor device. The apparatus includes a plurality of laser diode arrays that are configurable to provide an incident beam having different wavelength ranges. At least some of the laser diode arrays form two dimensional stacks that have different wavelength ranges from each other. The apparatus also includes optics for directing the incident beam towards the sample, a detector for generating an output signal or image based on an output beam emanating from the sample in response to the incident beam, and optics for directing the output beam towards the detector. The apparatus further includes a controller for configuring the laser diode arrays to provide the incident beam at the different wavelength ranges and detecting defects or characterizing a feature of the sample based on the output signal or image.

19 Claims, 7 Drawing Sheets

(51) Int. Cl.
*G01N 21/88* (2006.01)
*G03F 7/20* (2006.01)
*G01N 21/956* (2006.01)

(56) References Cited

U.S. PATENT DOCUMENTS

| | | | |
|---|---|---|---|
| 6,862,090 | B2 | 3/2005 | Chen et al. |
| 6,923,374 | B2 | 8/2005 | Knowles et al. |
| 6,937,754 | B1 | 8/2005 | Eguchi |
| 7,349,103 | B1 | 3/2008 | Balooch et al. |
| 7,405,417 | B2 | 7/2008 | Stevens et al. |
| 7,531,369 | B2 | 5/2009 | Venugopal |
| 7,755,775 | B1 | 7/2010 | Li |
| 7,826,047 | B2 | 11/2010 | Shibata et al. |
| 7,970,199 | B2 | 6/2011 | Yoshida et al. |
| 8,054,453 | B2 | 11/2011 | Harrison |
| 8,077,305 | B2 | 12/2011 | Owen et al. |
| 8,194,242 | B2 | 6/2012 | Derksen et al. |
| 2002/0195496 | A1 | 12/2002 | Tsikos et al. |
| 2003/0179369 | A1 | 9/2003 | Feldman et al. |
| 2004/0207836 | A1 | 10/2004 | Chhibber et al. |
| 2006/0158658 | A1 | 7/2006 | De Lega et al. |
| 2007/0097359 | A1 | 5/2007 | Engelbart et al. |
| 2007/0222974 | A1* | 9/2007 | Zhao et al. ............... 356/237.1 |
| 2008/0055897 | A1 | 3/2008 | Yoshida et al. |
| 2009/0002693 | A1 | 1/2009 | Engelbart et al. |
| 2010/0091272 | A1 | 4/2010 | Asada et al. |
| 2010/0189339 | A1 | 7/2010 | Amanullah et al. |
| 2011/0216792 | A1* | 9/2011 | Chann et al. ................ 372/31 |
| 2013/0342825 | A1 | 12/2013 | Chimmalgi et al. |

OTHER PUBLICATIONS

"U.S. Appl. No. 13/924,216, Notice of Allowance mailed Jul. 23, 2014", 8 pgs.

"EUV", Ushio Inc., 2010, 4 pgs.

"Int'l Application Serial No. PCT/US2013/047901, Search Report and Written Opinion mailed Sep. 30, 2013", 11 pgs.

"Light Emitting Diodes (LEDs) for General Illumination", OIDA, Oct. 2002, 111 pgs.

"Opto & Energy Solutions Newsletter", 37th Edition, Oct. 1, 2010, 25 pgs.

Clarke, T.A. et al., "The Use of Diode Laser Collimators for Targeting 3-D Objects.", Department of Electrical, Electronic and Information Engineering, City University, London, EC1V OHB, UK, 1994, 9 pgs.

Deninger, Anselm et al., "12 Orders of Coherence Control: Tailoring the coherence length of diode lasers", TOPTICA Photonics AG, Munich, Germany, Aug. 3, 2010, 1-8.

Engelhardt, Uli et al., "AlGaN UV-LEDs", Sommersemester, 2010, 19 pgs.

Glebov, Dr. Leonid , "Optimizing and Stabilizing Diode Laser Spectral Parameters", Photonics Spectra, Jan. 2005, 90-94.

Grandusky, James R. et al., "High Output Power from 260nm Pseudomorphic Ultraviolet Light-Emitting Diodes with Improved Thermal Performance", Applied Physics Express, vol. 4, 082101, 2011, 082101-1-082101-3.

Hirayama, Hideki et al., "222-282 nm AlGaN and InAlGaN based deep-UV LEDs fabricated on high-quality AlN template", Proceedings of SPIE, vol. 7216, 721621-2, 2009, 14 pgs.

Hirayama, Hideki et al., "222-282 nm AlGaN and InAlGaN-based deep-UV LEDs fabricated on high-quality AlN on sapphire", Phys. Status Solidi A 206, No. 6, 2009, 1176-1182.

Hirayama, Hideki , "Recent Progress of 220-280 nm-band AlGaN based deep-UV LEDs", Proceedings of SPIE, vol. 7617, 76171G-2, Retrieved from the Internet: < http://proceedings.spiedigitallibrary.org/ >, Accessed on Feb. 7, 2013, 2010, 11 pgs.

Khan, M. A. et al., "III—Nitride UV Devices", Japanese Journal of Applied Physics, vol. 44, No. 10, Oct. 2005, 7191-7206.

Khizar, M. et al., "Nitride deep-ultraviolet light-emitting diodes with microlens array", Applied Physics Letters, 86, 173504, 2005, 173504-173504-3.

Liao, Yitao et al., "AlGaN based deep ultraviolet light emitting diodes with high internal quantum efficiency grown by molecular beam epitaxy", Applied Physics Letter 98, 081110, Retrieved from the Internet: < http://dx.doi.org/10.1063/1.3559842 >, 2011, 4 pgs.

Liu, Chuan , "Implementation of Deep Ultraviolet Raman Spectroscopy", PhD Thesis, Technical University of Denmark, Dec. 2011, 172 pgs.

Oto, Takao et al., "100 mW Deep Ultraviolet Emission from AlGaN/AlN Quantum Wells by Electron Beam Pumping", Dept. of Electronic Science and Engineering, Kyoto University Katsura Campus, 2011, 5 pgs.

Oto, Takao et al., "100 mW deep-ultraviolet emission from aluminium-nitride-based quantum wells pumped by an electron beam", Dept. of Electronic Science and Engineering, Kyoto University, Ushio Inc., 2010, 35-39.

Pecora, Emanuele F. et al., "Polarization Properties of Deep-Ultraviolet Optical Gain in Al-Rich AlGaN Structures", Applied Physics Express, vol. 5, 032103, 2012, 032103-1-032103-3.

Pernot, Cyril et al., "Improved Efficiency of 255-280nm AlGaN-Based Light-Emitting Diodes", Applied Physics Express 3 (2010) 061004, 2010, 3 pgs.

Perrot, S. et al., "A versatile optical system for metrology and defects inspection of 3D integration processes", Retrieved from the Internet: < http://ieeexplore.ieee.org >, May 2012.

Schowalter, Leo J. , "Ultraviolet LEDs (My Excellent Adventure Starting a New Business)", Crystal IS, Inc., Accessed on Aug. 15, 2007, Retrieved from the Internet: < http://www.google.com/url?sa=t&rct=j&q=&esrc=s&frm=1&source=web&cd=1&ved=0CEUQFjAA&url=http%3A%2F%2Fwww.rpi.edu%2Fdept%2Fphys%2Fcourses%2FPHYS1010%2FSchowalter.pdf&ei=P3nEUcnkOoG49QTEiYCIDw&usg=AFQjCNFNVxEumxWzksJcOaVzt96lzr, 55 pgs.

Shatalov, Max et al., "Mercury-Free Solid State Deep UV Light Sources for Disinfection and Analysis", Sensor Electronic Technology, Inc.,, Retrieved from the Internet: < www.s-et.com >, Accessed on Jun. 20, 2013, 2 pgs.

Stephen, Mark A. et al., "Characterization of high-power quasi-cw laser diode arrays", NASA's Goddard Space Flight Center, Science Systems Applications, Inc., 2005, 12 pgs.

Tamulaitis, G. , "Ultraviolet Light Emitting Diodes", Lithuanian Journal of Physics, vol. 51, No. 3, 2011, 177-193.

Watanabe, Kenji et al., "DUV Optical Wafer Inspection System for 65-nm Technology Node", Hitachi Review vol. 54, No. 1, 2005, 23-26.

Wright, P.J. et al., "Design and application of Gray FieldTM technology for defect inspection systems", Retrieved from the Internet: < http://ieeexplore.ieee.org >, 2001.

Zhou, Wei et al., "Laser Dark-field Illumination System Modeling for Semiconductor", Presented at SPIE Optical System Design Conference, Marseilles, France, Sep. 2011, 5 pgs.

Zhu, Zhengrong et al., "METRO-3D: an efficient three-dimensional wafer inspection simulator for next-generation lithography", Retrieved from the Internet: < http://ieeexplore.ieee.org >, Nov. 2004.

* cited by examiner

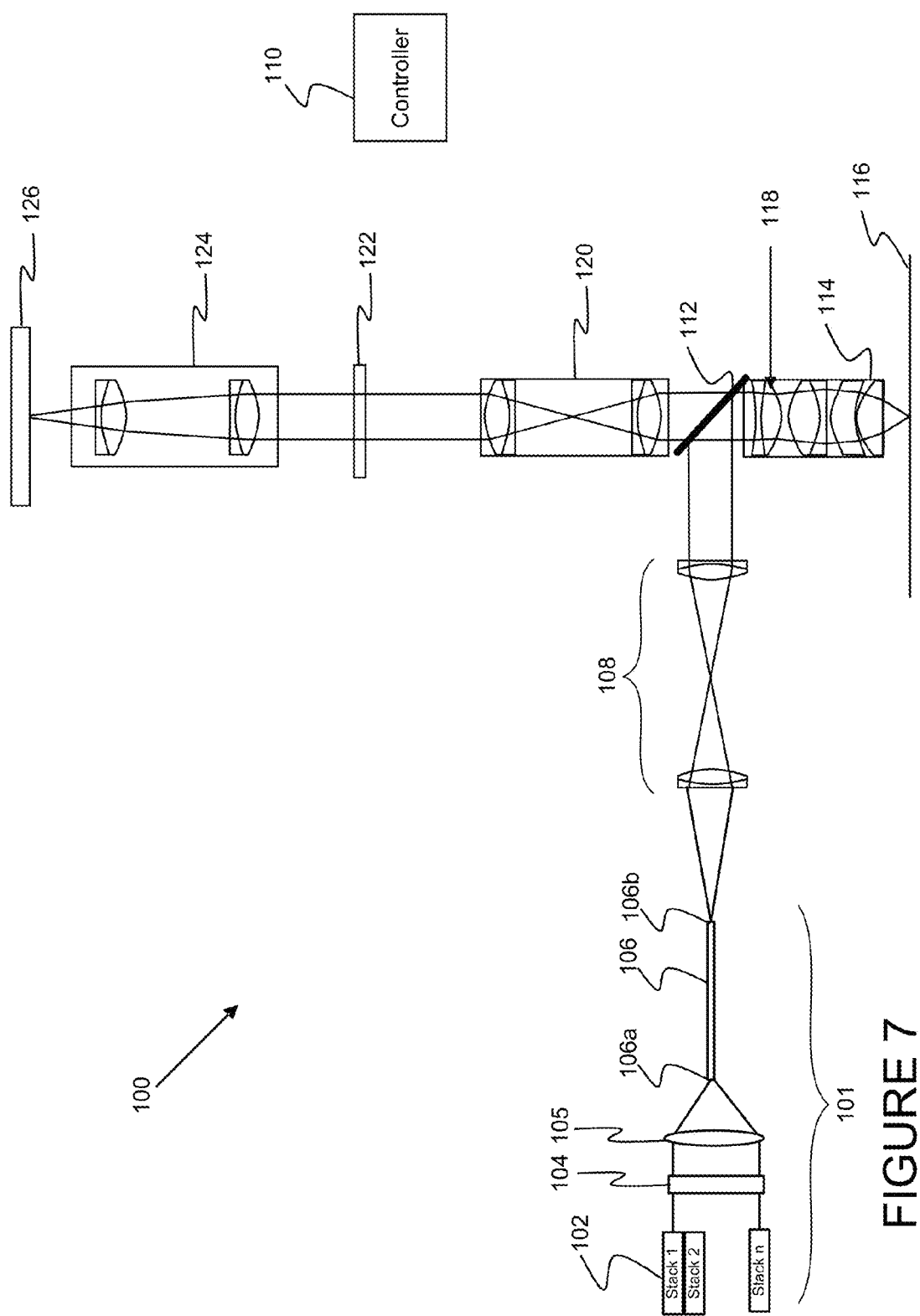

DIODE LASER BASED BROAD BAND LIGHT SOURCES FOR WAFER INSPECTION TOOLS

CROSS-REFERENCE TO RELATED APPLICATION

This application claims the benefit under 35 U.S.C. §120 to U.S. application Ser. No. 13/924,216, filed Jun. 21, 2013, titled "Diode Laser Based Broad Band Light Sources for Wafer Inspection Tools", by Anant Chimmalgi et al., which claims priority of U.S. Provisional Patent Application No. 61/664,493, entitled "Deep UV-UV-VIS-NIR Diode Laser Based Broad Band Light Sources for Wafer Inspection Tools", filed 26 Jun. 2012 by Anant Chimmalgi et al. Both applications are incorporated herein by reference in their entirety for all purposes.

TECHNICAL FIELD OF THE INVENTION

The invention generally relates to the field of wafer and reticle inspection and metrology. More particularly the present invention relates to the light sources of such inspection and metrology tools.

BACKGROUND

Generally, the industry of semiconductor manufacturing involves highly complex techniques for fabricating integrating circuits using semiconductor materials, which are layered and patterned onto a substrate, such as silicon. An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer.

Due to the large scale of circuit integration and the decreasing size of semiconductor devices, the reticles and fabricated devices have become increasingly sensitive to defects. That is, defects which cause faults in the device are becoming increasingly smaller. The device can generally be required to be fault free prior to shipment to the end users or customers.

Various inspection and metrology systems are used within the semiconductor industry to detect defects or characterize structures on a semiconductor reticle or wafer. One type of tool is an optical inspection or metrology system. In optical inspection and metrology systems, one or more incident beams are directed towards the semiconductor wafer or reticle and a reflected and/or scattered beam is then detected. The detected beam is used to then generate a detected electrical signal or an image, and such signal or image is then analyzed to determine whether defects are present on the wafer or reticle or characterize features on the sample under test.

Various light source mechanisms can be used with optical inspection and metrology tools. One example is an arc lamp based light source. Another example is a laser sustained plasma light source. Both an arc lamp and plasma based light source tend to produce a significant amount of out-of-band radiation, which leads to poor power conversion efficiency. Additionally, these light sources require complex thermal heat management mechanisms for the out-of-band radiation. The plasma based light source also has limits on power brightness scalability.

There is a continuing need for improved light sources for optical inspection and metrology tools.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, an optical apparatus for performing inspection or metrology of a semiconductor device is disclosed. The apparatus includes a plurality of laser diode arrays that are configurable to provide an incident beam having different wavelength ranges. At least some of the laser diode arrays form two dimensional stacks that have different wavelength ranges from each other. The apparatus also includes optics for directing the incident beam towards the sample, a detector for generating an output signal or image based on an output beam emanating from the sample in response to the incident beam, and optics for directing the output beam towards the detector. The apparatus further includes a controller for configuring the laser diode arrays to provide the incident beam at the different wavelength ranges and detecting defects or characterizing a feature of the sample based on the output signal or image.

In a specific implementation, the laser diode arrays include deep UV (ultra-violet) and UV continuous wave diode lasers. In one aspect, the laser diode arrays further include VIS (visible) and NIR (near infrared) continuous wave diode lasers. In yet a further aspect, the 2D stacks are formed from diode bars that can be selectively activated to result in the incident beam having different wavelength ranges that together form a broadband range.

In another embodiment, the controller is configured to activate one or more laser diode arrays so that the incident beam has a specific wavelength range that is selected from the different wavelength ranges and configured to deactivate other one or more of the laser diode arrays so that the incident beam does not include any wavelengths that are not within the specific wavelength range. In a further aspect, the apparatus includes beam shaping optics for receiving output light from the activated one or more laser diode arrays and forming different illumination profiles in the incident beam. In another aspect, the apparatus includes coupling optics for receiving and combining output light from the activated one or more laser diode arrays. In one example implementation, the coupling optics comprises a spatial coupler or polarization coupler to combine output light having a same wavelength so as to achieve a higher net power than a power of individual diodes or diode bars of the laser diode arrays and a wavelength coupler for combining output light having different wavelength ranges.

In a specific embodiment, the 2D stacks are formed from diode bars. For example, the wavelength ranges of the stacks together cover a range between about 190 nm and about 1000 nm. In one aspect, the wavelength ranges of the stacks together include wavelengths in the deep UV, UV, VIS, and NIR. In another aspect, a first set of one or more 2D stacks is formed from deep UV or UV based laser diodes; a second set of one or more 2D stacks is formed from VIS based laser diodes; and a third set of one or more 2D stacks is formed from deep NIR based laser diodes. In yet another embodiment, each 2D stack has a wavelength range width that is between about 15 to 80 nm. Each laser diode of each diode bar can provide about 1 watt or more of power. In one example, each 2D stack provides about 200 watts or more of power. In another implementation, the diode bars of each 2D stack have a same wavelength range as its corresponding 2D stack.

These and other aspects of the invention are described further below with reference to the figures.

BRIEF DESCRIPTION OF THE DRAWINGS

FIG. 7 is a diagrammatic representation of an inspection system, in which embodiments of illumination source module with configurable diode laser arrays, may be integrated in accordance with a specific implementation of the present invention.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

In general, an illumination source having configurable incoherent laser diode arrays (e.g., 2-D stacks of emitters) for use in an optical inspection tool is provided. The illumination source includes laser diode arrays that are configurable to cover specific ranges of wavelengths as needed in the particular inspection application. For instance, the laser diode arrays provide wavelength widths that are selectively obtained from the Deep-UV (ultra-violet), UV, VIS (visible), and NIR (near-infrared) range.

Figure 1:
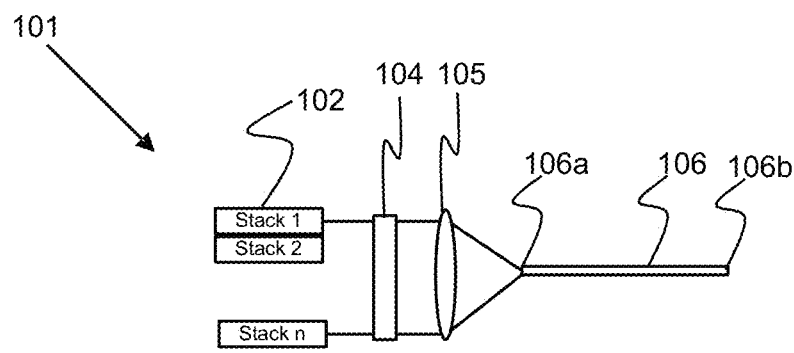
FIG. 1 is a diagrammatic representation of an illumination source arrangement having configurable diode arrays in accordance with one embodiment of the present invention.

FIG. 1 is a diagrammatic representation of an illumination source arrangement 101 having configurable diode arrays in accordance with one embodiment of the present invention. As shown, the illumination source arrangement 101 includes a plurality of illumination sources 102. In the illustrated implementation, each illumination source 102 is in the form of a plurality of configurable 2D stacks of laser emitter diodes (e.g., Stacks 1-n) although each illumination source could simply be in the form of a 1D array of emitter diodes.

The illumination source arrangement 101 may also include beam shaping optics 104 for manipulating the profile of one or more of the beams output by the active diodes and beam coupling optics 105 for coupling the beams output from the active illumination sources together. In the illustrated embodiment, the beam shaping optics 104 are arranged adjacent to the illumination sources so as to directly receive and shape one or more of the beams that are output from the illumination sources. Alternatively, the beam coupling optics 105 may be arranged adjacent to the illumination sources so as to directly receive and couple the beams output from the illumination sources prior to the coupled beam being received by the beam shaping optics 104. In yet another alternative, different portions of the beam shaping optics 104 and/or the beam coupling optics 105 may be placed in different paths from different subsets of the beams output from the active diodes.

The illumination source arrangement 101 may also include a homogenizer 106 for receiving the coupled, shaped resulting beam that is output from the beam coupling optics 105 and the beam shaping optics 104. The coupled and/or shaped incident beam passes through a first end of 106a the homogenizer 106 and may be output through a second end 106b of such homogenizer 106 to provide incident light for a particular inspection or metrology system as described further below.

Although the illustrated illumination source module 101 is described as comprising shaping optics 104, beam coupling optics 105, and homogenizer 106, it is understood that one or more of these components could be integrated in other modules of an optical inspection or metrology tool. For instance, the illumination source module 101 may not include a homogenizer so that the output of the beam shaping optics 105 is produced onto the input of an optical tool's homogenizer or another suitable optical component of such optical system.

Referring back to FIG. 1, one or more illumination sources 102 may be selectively turned on to output one or more beams that can be coupled onto a first fiber end 106a. In some configurations, one or more other illumination source 102 may be turned off so as to be prevented from outputting a beam that is coupled and/or shaped onto the first fiber end 106a to produce an incident beam. Each illumination source may be selectively activated simultaneously, sequentially, or in any suitable order.

Figure 2A:
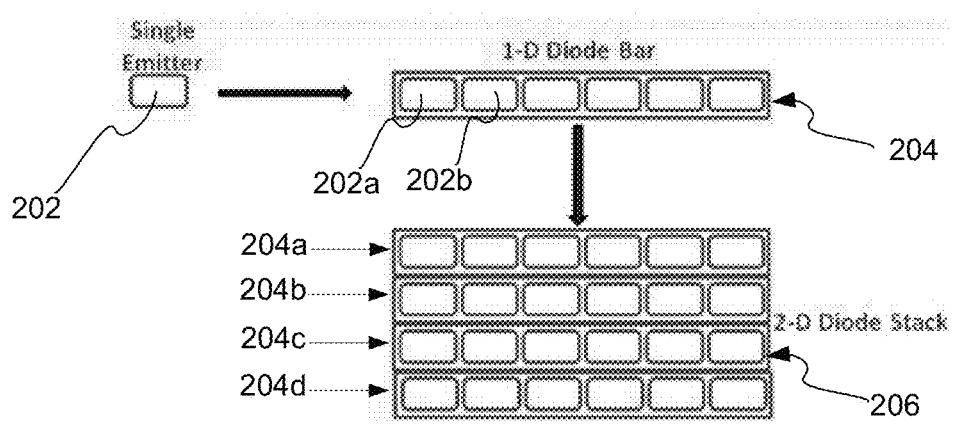
FIG. 2A is a diagrammatic representation of forming a 2D stack from individual emitter diodes in accordance with a specific implementation of the present invention.

FIG. 2A is a diagrammatic representation of a 2D diode stack 206 in accordance with a specific implementation of the present invention. As shown, a 1D diode bar 204 is formed from individual emitter diodes (e.g., 202, 202a, 202b), and a plurality of 1D diode bars (e.g., 204a, 204b, 204c, and 204d) are used to form 2D diode stack 206. In one example, continuous wave emitters may be used to form 2D diode stacks. Each emitter diode may be in the form of an edge type emitter so that the output is propagated along the wafer surface and out a cleaved side edge of the diode.

In general, the diode material can be altered so as to generate different wavelength ranges for the diode output. Each 2D stack can be formed from diode bars that have the same or different wavelength characteristics. The different stacks, and optionally the different diode bars of one or more stacks, can cover different wavelength widths or ranges. The stacks can then selectively cover a wide range of wavelengths for various applications. For instance, if all of the diode stacks were activated, they would together produce light having a wavelength range of about 190 to 1000 nm, or even as low as 100 nm. For instance, a first set of bars or stacks may be formed from different DUV-UV based diodes; a second set of bars or stacks can be formed from different VIS based diodes; while a third set of bars or stacks can be formed from different NIR based diodes.

Deep UV and UV based diodes in wavelength ranges of about 220 nm to about 330 nm have been developed by numerous companies and institutes, such as RIKEN Advanced Science Institute of Japan. These Deep UV and UV based diodes from RIKEN have a maximum output power is 33 mW for a 270 nm DUV-LED, by way of specific example. For diodes with wavelength shorter than 260 nm, the output powers are 15 mW and 5 mW for 247 nm and 237 nm DUV-LEDs, respectively. VIS and NIR based diodes, bars, and stacks having power in the 10's of mW's are available from Oclaro of San Jose, Calif.

In a specific example with respect to FIG. 1, stack 1 has a wavelength range of X+5 nm to X+10 nm, and stack 2 has a wavelength range of X+15 nm to X+20 nm. If X equals 190 nm and portions of the range between 190 nm and 1000 nm are to be selectively covered, the remaining stacks each have different ranges, up to X+810 nm for stack n. Each stack of this arrangement can be formed from 1D diode bars that each has the same wavelength range as its stack. A stack's individual bars may have the same wavelength range to achieve a particular power requirement. Otherwise, a stack's individual bars may have different wavelength widths if the power requirements are met by a single bar. For instance, a first bar 204a of stack 206 (FIG. 2) has a first width of X+5 nm to X+10 nm, and a second bar 204b of stack 206 has a wavelength range of X+15 nm to X+20 nm. A third bar 204c of stack 206 has a first width of X+20 nm to X+25 nm, and the remaining bars of this stack 206, as well as other stacks, can have different widths, up to X+810 nm if the same example maximum width of 190 nm to 1000 nm is used.

Individual diodes or 1D diode bars may have as low as a 5-10 nm wide bandwidth and a power range between about 10's of mW's and 100's of mW's. In one embodiment, each diode provides 1 W (Watt) or more of power so that a 2D stack having up to 200 W can be achieved by arranging up to 200 diodes in the bars of each stack. Multiple 200 W stacks can be coupled together to form a broadband incoherent laser based light source in one inspection application, which can be very attractive for bright field tools as an alternate for laser sustained plasma sources that can only achieve kW's of power. Integrating such emitters into 2-D stacks will make it possible to get this high power output in a small wavelength spread (~3 nm FWHM) that can be coupled into a 1 mm diameter delivery fiber with 0.24 NA, by way of example.

Regardless of each particular diode bar or stack arrangement, each selectable subset of diodes (bar or stack) can have a 15-80 nm wavelength width, which can be selectively activated and combined into wider widths. These arrangements allow particular wavelengths to be turned on or off on demand, depending on the particular layer being inspected and the kind of defect. The laser power of the activated light sources can also be directly modulated, depending on the wafer type, resulting in an efficient light source with reduced illuminator thermal management concerns. That is, complex thermal management mechanisms are not needed.

Figure 2B:
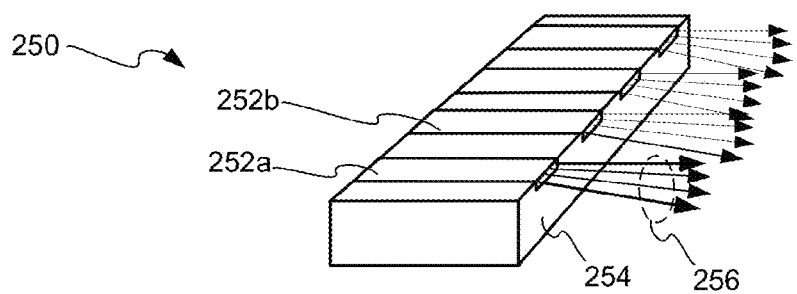
FIG. 2B is a perspective view of an edge-emitting laser diode bar in accordance with a specific implementation of the present invention.

The 1D or 2D diode arrays described herein may have any suitable construction. In general, each laser diode includes a current-carrying p-n or p-i-n semiconductor junction, in which holes recombine to release energy as photons. The photons can be emitted perpendicular to the semiconductor surface (surface emitting diode) or emitted from a cleaved edge (edge-emitting diode). FIG. 2B is a perspective view of a laser diode bar 250 having a plurality of waveguides (e.g., 252a and 252b) for outputting light (e.g., 256) for each diode at a cleaved edge 254 of the diode bar.

Figure 2C:
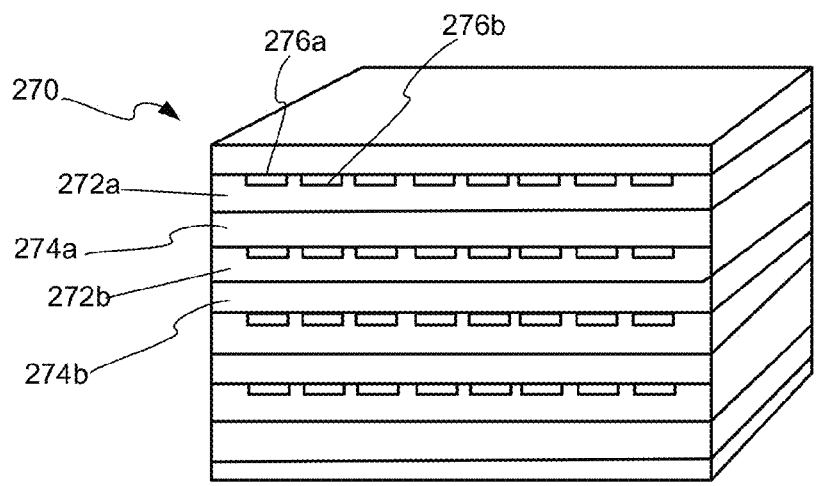
FIG. 2C is a perspective view of an edge-emitting laser diode stack in accordance with a specific implementation of the present invention.

Each stack may then be formed from 1D arrays of edge emitter diodes as shown in FIG. 2C. As shown, the stack 270 may be formed from alternating 1D diode bars (e.g., 272a and 272b) and heat sink layers (e.g., 274a and 274b). Each 1D diode bar can be configurable to edge-emit light from waveguides (e.g., 276a and 276b). In a specific example, each stack may be fabricated by cleaving 1D laser arrays from a wafer. Each 1D laser array is attached to a thin heat sink layer. The sets of 1D array and heat sink layer are then attached together to form alternating array and heat sink layers. The width and height of each stack can be selected based on the particular aperture, delivery fiber width, and NA of the inspection system.

The output of two or more of the active 1D or 2D diode arrays can be coupled to any suitable type of coupler, such as a spatial coupler, polarization coupler, a wavelength coupler, or any combination thereof. The first two coupling types can be used to increase the net output from a laser at a particular wavelength, while the wavelength coupling type may be used to achieve a more broadband source with multiple wavelengths that are simultaneously coupled into the delivery path.

Figure 3A:
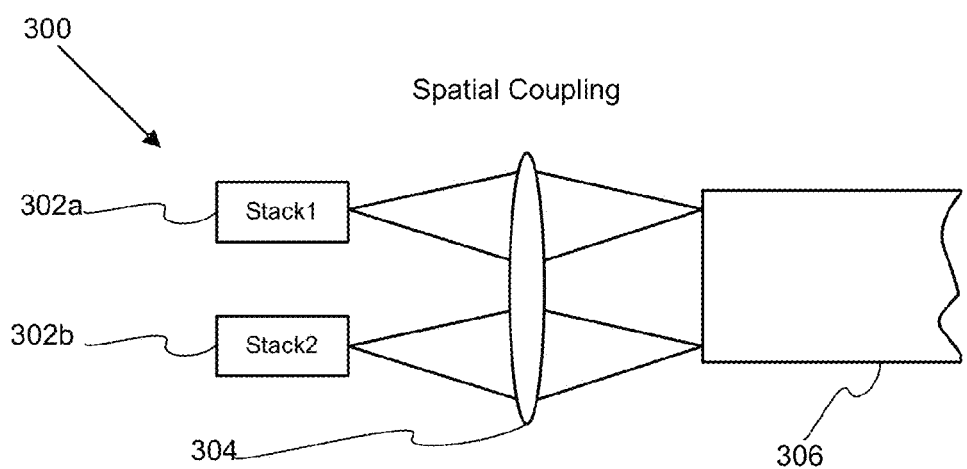
FIG. 3A is a diagrammatic representation of spatial coupling optics for coupling the outputs of configurable diode arrays in accordance with one embodiment of the present invention.
Figure 3B:
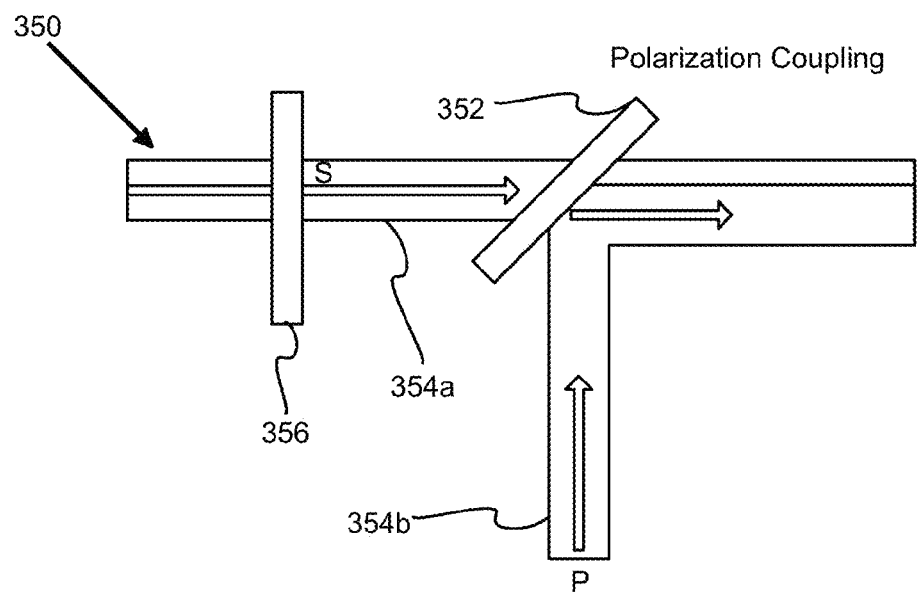
FIG. 3B is a diagrammatic representation of a polarization coupling optics arrangement for coupling the outputs of configurable diode arrays in accordance with one embodiment of the present invention.
Figure 3C:
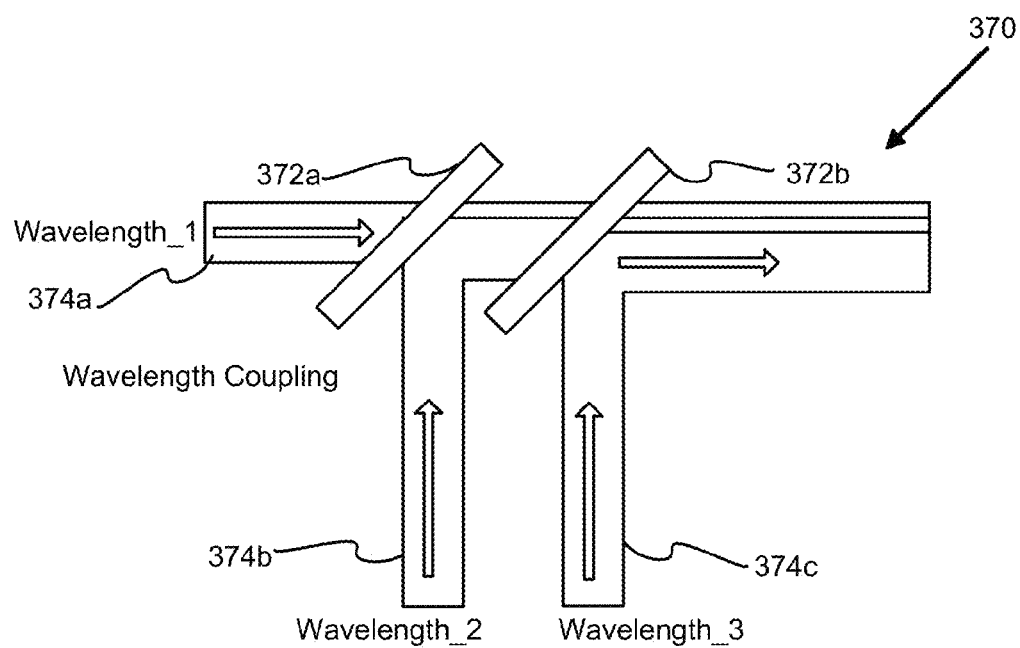
FIG. 3C is a diagrammatic representation of a wavelength coupling optics arrangement for coupling the outputs of configurable diode arrays in accordance with a first implementation.

FIGS. 3A-3C illustrate these different ways to combine the output of 2D diode stacks. FIG. 3A is a diagrammatic representation of a spatial coupling optics arrangement 300 for coupling the outputs of configurable diode arrays in accordance with one embodiment of the present invention. As shown, the output of stack1 302a and stack2 302b are both received by spatial coupling optics 304, which is configured to spatially combine the two beams so that such beams are delivered onto a portion of the delivery path, e.g., fiber 306. For example, spatial coupling optics 304 directs the output of stack1 302a to the top half of optical fiber 306 and directs the output of stack2 302b to the lower half of optical fiber 306. The fiber mixes the received light together. The spatial coupling optics may take the form of individual fibers that are fed into a larger light pipe or fiber. The large fiber mixes the light.

Although the output from the spatial coupling optics is shown as being directly received by optical fiber 306, other coupling optics may be interposed between the spatial coupling optics 304 and the fiber 306. Additionally, any set of activated one or more stacks may be spatially coupled onto the delivery path.

FIG. 3B is a diagrammatic representation of a polarization coupling optics arrangement 372 for coupling the outputs of configurable diode arrays in accordance with one embodiment of the present invention. As shown, an S polarizer 356 is arranged to receive the output from a first stack (not shown) and output S polarization 354a. A polarization coupler 352 is then arranged to receive the P polarization output 354b from a second stack (not shown) and couple the S and P polarization outputs together.

FIG. 3C is a diagrammatic representation of a wavelength coupling optics arrangement 370 for coupling the outputs of configurable diode arrays in accordance with a first implementation. In this embodiments, the wavelength coupling optics are formed from dichroic mirrors that each transmit a first wavelength and reflect a second wavelength. As illustrated, output 374a (from a first diode array) having a first wavelength_1 is transmitted by mirror 372a, while output 374b (from a second array) having a second wavelength_2 is reflected by mirror 372a. Thus, the two outputs having wavelength_1 and wavelength_2 are combined by mirror 372a. A second mirror 372b is then arranged to receive and transmit the combined beams and reflect a third output 374c (from a third diode array) having a third wavelength_3 so that the three outputs 374a~c having three wavelengths_1~3 are combined together. Any number of mirrors may be successively arranged to combine any number of wavelength outputs from different diode arrays. The mirrors are configured to transmit and reflect the corresponding wavelength ranges of the received diode bar or stack outputs.

Figure 3D:
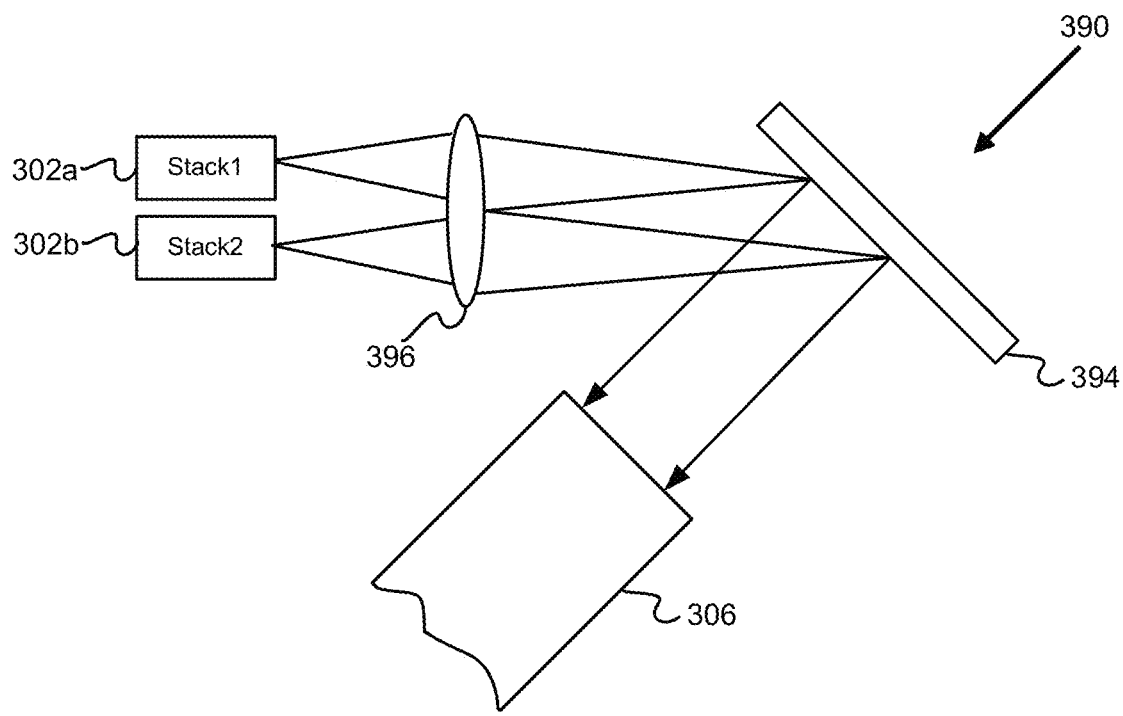
FIG. 3D is a diagrammatic representation of a wavelength coupling optics arrangement for coupling the outputs of configurable diode arrays in accordance with a second implementation.

FIG. 3D is a diagrammatic representation of a wavelength coupling optics arrangement 370 for coupling the outputs of configurable diode arrays in accordance with a second implementation. In this embodiment, a diffraction grating coupler 394 receives the output from stack1 302a and stack2 302b via spatial coupler 396 at different angles and combines the received light into one beam, which is then received onto the delivery path, e.g., fiber 306. Finer grained wavelength widths for each diode array can be achieved with diffraction couplers.

Figure 4:
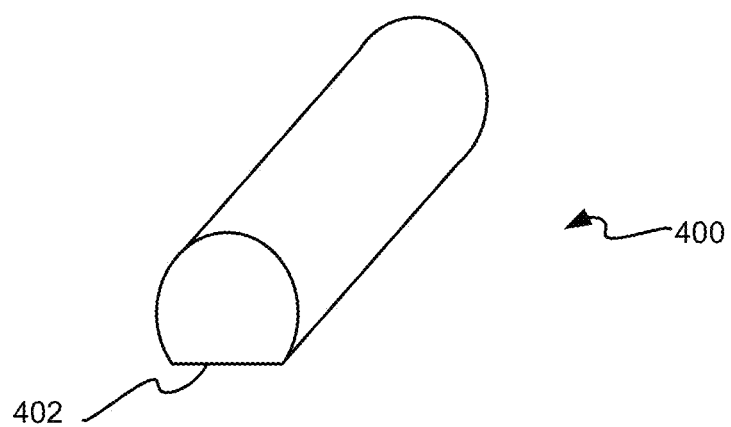
FIG. 4 illustrates a homogenizer in the form of an optical fiber having a single flat facet.

In specific embodiments, the coupled output may be received by a homogenizer that takes the form of one or more of the following components: an optical fiber having one or more faceted edges, micro-lens or micro-prism arrays that are combined with or without light pipes, etc. FIG. 4 illustrates a homogenizer 400 in the form of an optical fiber having a single flat facet 402. Alternatively, the optical fiber could have multiple faceted edges.

Figure 5:
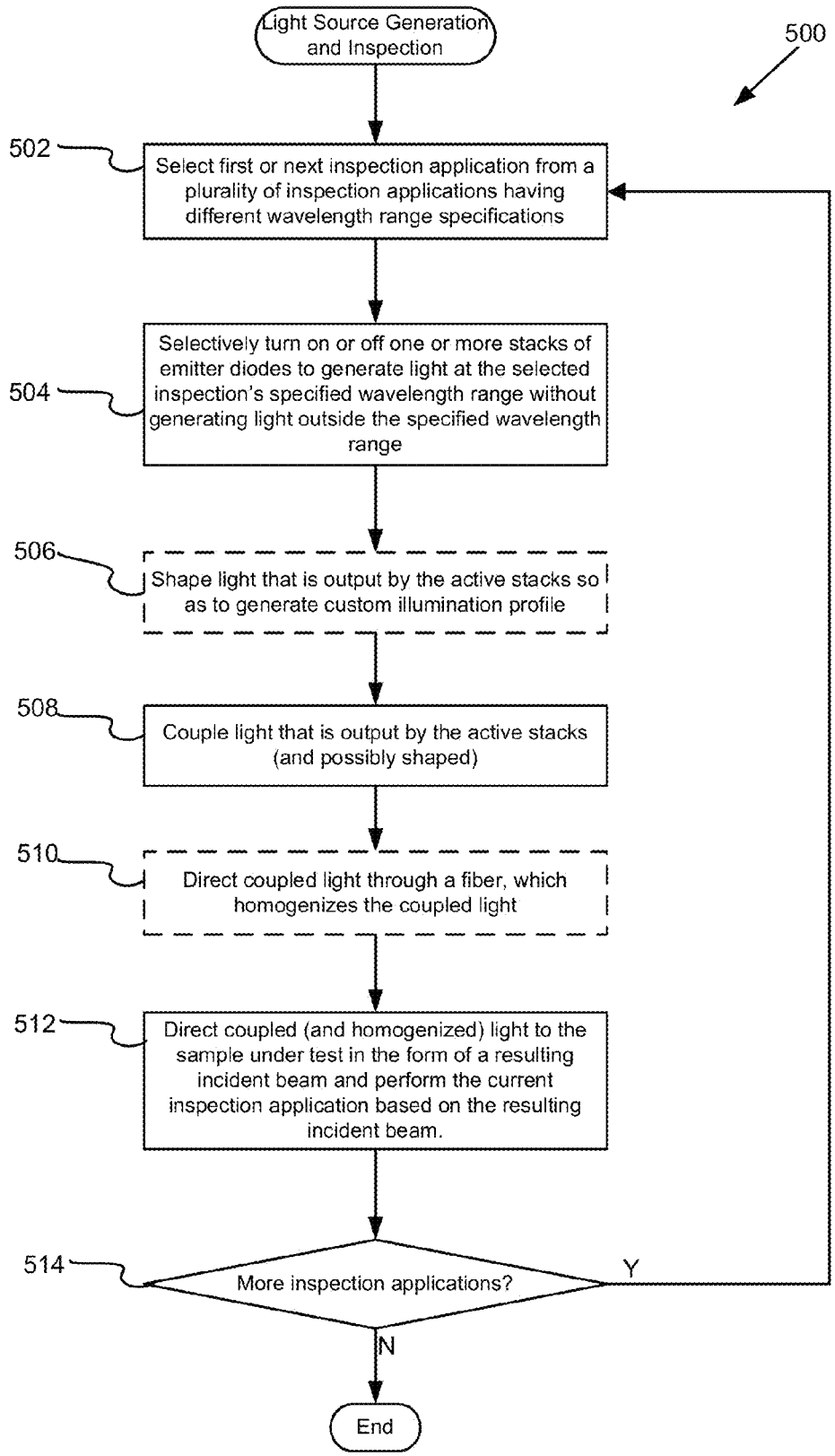
FIG. 5 is a flow chart illustrating a procedure for light source generation and inspection/metrology in accordance with one embodiment of the present invention.

FIG. 5 is a flow chart illustrating a procedure 500 for light source generation and inspection (or metrology) in accordance with one embodiment of the present invention. Initially, a first inspection application may be selected from a plurality of different inspection applications having different wavelength range specifications in operation 502. For instance, a deep UV inspection may be selected. One or more stacks (or bars) of emitter diodes may then be selected to generate light at the selected inspection's specified wavelength range without generating light outside the specified wavelength range in operation 504. For instance, only stacks (or bars) that are configured to emit deep UV are activated, while other stacks having VIS or NIR wavelength ranges are kept off or turned off.

Figure 6A:
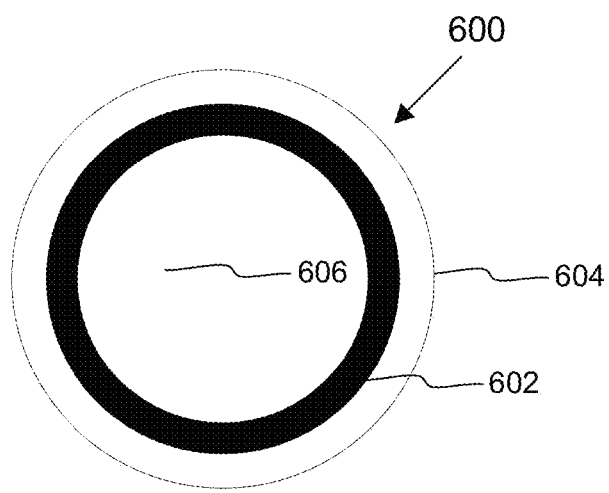
FIGS. 6A through 6C represent different illumination profiles that can be produced at the pupil plane by embodiments of the present invention.
Figure 6B:
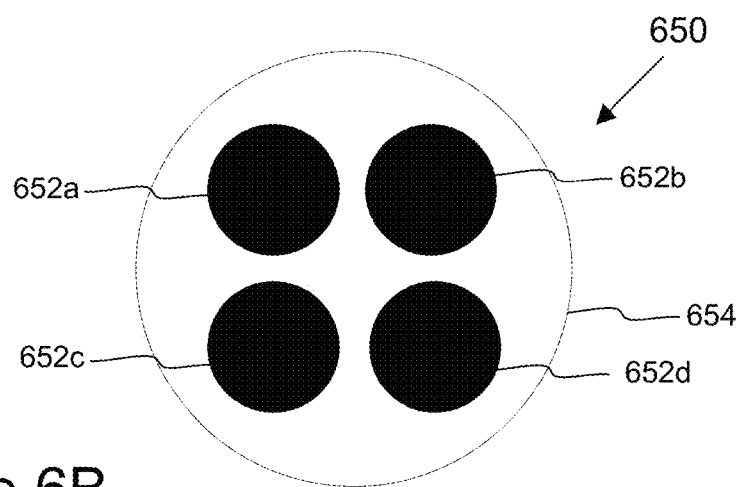
Figure 6C:
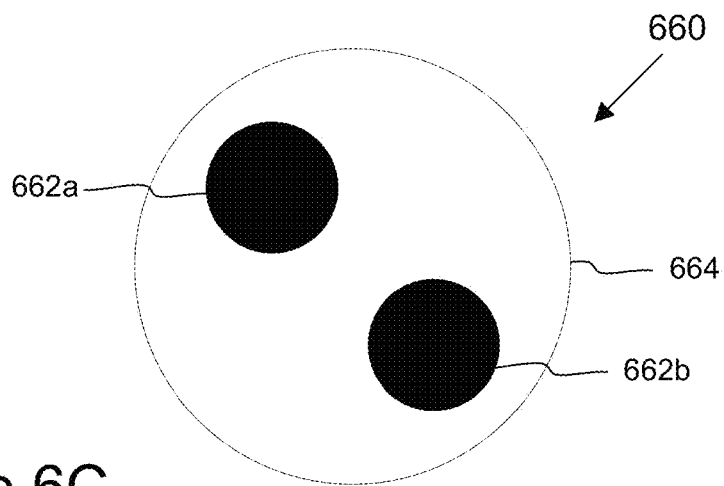

The light that is output by the active stacks (or bars) may then be shaped so as to generate custom illumination profiles in operation 506. This customization is optional. FIGS. 6A through 6C represent different illumination profiles that can be produced at the pupil plane of the optical tool using light source embodiments of the present invention. The incident beam cross section at the pupil plane is represented by the dark sections. Of course, other types of illuminations profiles may be generated with the present invention.

FIG. 6A shows pupil plane 600 with an annular illumination profile for the beam. That is, only an annular portion 602 of the incident beam is generated at the pupil 600, while portions 604 and 606 of the incident beam are not. FIG. 6B illustrates pupil plane 650 with a quadrapole illumination profile for the incident beam. That is, only quadrapole portions 652a through 652d of the incident beam are generated at the pupil 650, while portion 654 of the incident beam is not. FIG. 6C illustrates pupil plane 660 with a dipole illumination profile for the incident beam. That is, only dipole portions 662a and 662b of the incident beam are generated at the pupil 650, while portion 664 of the incident beam is not.

Additionally, output from different wavelength width stacks (or bars) may be directed to different portions of the pupil area so as to result in different angles of incidence. For instance, each of the quadrapole portions of FIG. 6B or the dipole portions of FIG. 6C may be arranged to receive a stack (or bar) output beam having a different wavelength range.

Referring back to FIG. 5, the light that is output by the active stacks (or bars), and possibly shaped, may then be coupled together in operation 508. For example, a spatial, polarization, and/or wavelength coupler is arranged in the path of light output by two or more stacks (or bars). This coupling can also be arranged to work in conjunction with any shaping optics so as to achieve different stack (or bar) outputs being directed to different portions of a particular the illumination profiles.

The coupled light may then be optionally directed through a fiber, which homogenizes the coupled light, in operation 510. The coupled (and possibly homogenized) light may then be directed to the sample under test in the form of a resulting incident beam and the currently selected inspection application is performed based on the resulting incident beam in operation 512. For instance, light emanating from the sample in response to the incident light is detected and analyzed to determine characteristics of the sample, such as a semiconductor wafer or reticle.

It may then be determined whether there are more inspection applications in operation 514. If there are no more inspections to be performed, for example, using different wavelength ranges, the procedure 500 may end. Otherwise, a next inspection application may then be selected and the procedure 500 repeats. For instance, a VIS based inspection application is selected, and the diode arrays that emit VIS wavelengths are activated, while other diode arrays that emit non VIS wavelengths are deactivated or left off.

Certain embodiments of the present invention provide customizable light source activation and generation to a beam coupler that outputs a single beam having a broad enough or "just right" wavelength range. This customizable light source can meet a diverse number of light source needs for different inspection or metrology applications at relatively high power levels. The use of multiple illuminations diode array sources allows efficient delivery of high brightness illumination to the sample. Lasers with different wavelengths can be efficiently combined. This arrangement is especially suited for dark field inspection, where an increase in light efficiency is highly desired to detect increasingly smaller surface anomalies. Additionally, different imaging and inspection modes (such as bright field and dark field inspection modes) may be readily provided simply by selectively lighting different fibers.

The illumination source embodiments of the present invention may be implemented in any suitable inspection or metrology tool and configured to provide selected wavelength ranges for a diverse number and type of inspection or metrology applications. FIG. 7 is a diagrammatic representation of an inspection or metrology system 100, in which embodiments of illumination source module 101 with configurable diode laser arrays, may be integrated in accordance with a specific implementation of the present invention. As shown, the system 100 includes the illumination source arrangement 101 of FIG. 1, which includes 2D diode array stacks 102 that are each configurable to be turned on (active) or off (inactive).

The system 100 also includes a controller 110 for causing selected ones of the illumination sources 102 to be turned on or off.

The incident beam may pass from the homogenizer 106 through a number of lenses 108, which serve to relay the beam(s) towards a sample 116. These lenses 108 may provide any suitable beam manipulation function on the incident beam, such as collimating, converging, expanding, reducing, etc. The incident beam may then be received by beam splitter 112 which then reflects the incident beam through objective lens 114, which focuses the incident beam onto sample 116 at one or more incident angles. For instance, the second homogenizer end 106b is imaged onto the back focal plane 118 of the objective lens 114.

The homogenizer 106 may take the form of a fiber 106 and be coupled with a fiber modulator (not shown), which operates to substantially eliminate the speckle noise which may be present in the incident beam to thereby produce a more uniform, incoherent illumination. For example, the fiber modulator may be a piezoelectric modulator which operates to stretch the homogenizer fiber so as to change the phase difference between the modes inside the fiber to therefore reduce the spatial coherence to produce a speckle free illumination. The system may alternatively or additionally include rotating diffuser to reduce speckle. However, a rotating diffuser also has low light efficiency and may only be used for applications which do not require high light efficiency, such as bright field inspection.

After the incident beam impinges on the sample, the light may then be reflected (and/or transmitted) and scattered from the sample 116, which is referred to herein as "output beam" or "output light", which may include any number of rays or beamlets. The inspection system also includes any suitable lens arrangements for directing the output light towards a detector. In the illustrated embodiment, the output light pass through beam splitter 112, Fourier plane relay lens 120, imaging aperture 122, and zoom lens 124. The Fourier plane relay lens generally relays the Fourier plane of the sample to the imaging aperture 122. The imaging aperture 122 may be configured to block portions of the output beam. For instance, the aperture 122 may be configured to pass all of output light within the objective numerical aperture in a bright field inspection mode, and configured to pass only the scattered light from the sample during a dark field inspection mode. A filter may also be placed at the imaging aperture 122 to block higher orders of the output beam so as to filter periodic structures from the detected signal.

After going through the imaging aperture 122, the output beam may then pass through zoom lens 124, which serves to magnify the image of the sample 116. The output beam then impinges upon detector 126. Suitable sensors include charged coupled devices (CCD), CCD arrays, time delay integration (TDI) sensors, TDI sensor arrays, photomultiplier tubes (PMT), and other sensors. In a reflecting system, optical elements would illuminate the sample and capture the reflected image.

The controller 110 may be any suitable combination of software and hardware and is generally configured to control various components of the inspection system 100. For instance, the controller may control selective activation of the illumination sources 102, fiber modulator settings, the imaging aperture 122 settings, etc. The controller 110 may also receive the image or signal generated by the detector 126 and be configured to analyze the resulting image or signal to determine whether defects are present on the sample, characterize defects present on the sample, or otherwise characterize the sample by determining sample parameters.

Example sample parameters that can be determined based on one or more detected signals or images include critical dimension (CD), film thickness, metal gate recess, high k recess, side wall angle, step height, pitch walking, trench and contact profile, overlay, material properties (e.g., material composition, refractive index, stress on critical films, including ultra-thin diffusion layers, ultra-thin gate oxides, advanced photoresists, 193 nm ARC layers, ultra-thin multilayer stacks, CVD layers, and advance high-k metal gate (HKMG), ultra-thin decoupled plasma nitridation (DPN) process layers, stress on noncritical films, including inter-dielectrics, photoresists, bottom anti-reflective coatings, thick oxides and nitrides, and back end of line layers), semiconductor manufacturing process parameters (e.g. focus and dose for scanners, etch rate for etching tools), etc.

Referring back to FIG. 7, the second end of 106b of the homogenizer 106 may be preferably positioned such that the pupil plane of the objective lens is imaged at the second end 106b. That is, the second homogenizer ends 106b is positioned within the illumination pupil, which is the conjugate plane of the objective back focal plane 118. The second homogenizer end 106b may be arranged to transmit any particular shape (e.g., produced by the beam shaper optics 105) so as to illuminate a particular one- or two-dimensional area of the sample 116 at one or more incident angles.

The controller 110 may be configured (e.g., with programming instructions) to provide a user interface (e.g., on a computer screen) for displaying resultant test images and other inspection characteristics. The controller 110 may also include one or more input devices (e.g., a keyboard, mouse, joystick) for providing user input, such as selecting wavelength ranges of incident light. In certain embodiments, the controller 110 is configured to carry out light source activation and inspection techniques. The controller 110 typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

It should be noted that the above diagrams and description are not to be construed as a limitation on the specific components of the system and that the system may be embodied in many other forms. For example, it is contemplated that the inspection or measurement tool may be any of a number of suitable and known imaging or metrology tools arranged for resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may be contemplated.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. An optical apparatus for performing inspection or metrology of a semiconductor device, comprising:
    a plurality of laser diode arrays that are configurable to provide an incident beam having different wavelength ranges, wherein at least some of the laser diode arrays form two dimensional (2D) stacks that have different wavelength ranges from each other, wherein a first set of one or more of the 2D stacks is formed from deep UV or UV based laser diodes, a second set of one or more of the 2D stacks is formed from VIS based laser diodes, and a third set of one or more of the 2D stacks is formed from deep NIR based laser diodes;
    optics for directing the incident beam towards the sample;
    a detector for generating an output signal or image based on an output beam emanating from the sample in response to the incident beam;
    optics for directing the output beam towards the detector; and
    a controller for configuring the laser diode arrays to provide the incident beam at the different wavelength ranges and detecting defects or characterizing a feature of the sample based on the output signal or image.

2. The apparatus of claim 1, wherein the 2D stacks are formed from diode bars that can be selectively activated to result in the incident beam having different wavelength ranges that together form a broadband range.

3. The apparatus of claim 1, wherein the controller is configured to activate one or more laser diode arrays so that the incident beam has a specific wavelength range that is selected from the different wavelength ranges and configured to deactivate other one or more of the laser diode arrays so that the incident beam does not include any wavelengths that are not within the specific wavelength range.

4. The apparatus of claim 3, further comprising beam shaping optics for receiving output light from the activated one or more laser diode arrays and forming different illumination profiles in the incident beam.

5. The apparatus of claim 3, further comprising coupling optics for receiving and combining output light from the activated one or more laser diode arrays.

6. The apparatus of claim 5, wherein the coupling optics comprises a spatial coupler or polarization coupler to combine output light having a same wavelength so as to achieve a higher net power than a power of individual diodes or diode bars of the laser diode arrays and a wavelength coupler for combining output light having different wavelength ranges.

7. An optical apparatus for performing inspection or metrology of a semiconductor device, comprising:
    a plurality of laser diode arrays that are configurable to provide an incident beam having different wavelength ranges, wherein at least some of the laser diode arrays form two dimensional (2D) stacks that have different wavelength ranges from each other, wherein the 2D stacks are formed from diode bars;
    optics for directing the incident beam towards the sample;
    a detector for generating an output signal or image based on an output beam emanating from the sample in response to the incident beam;
    optics for directing the output beam towards the detector; and
    a controller for configuring the laser diode arrays to provide the incident beam at the different wavelength ranges and detecting defects or characterizing a feature of the sample based on the output signal or image.

8. The apparatus of claim 1, wherein the wavelength ranges of the 2D stacks together cover a range between about 190 nm and about 1000 nm.

9. The apparatus of claim 1, wherein the wavelength ranges of the 2D stacks together include wavelengths in the deep UV, UV, VIS, and NIR.

10. The apparatus of claim 1, wherein each 2D stack has a wavelength range width that is between about 15 to 80 nm.

11. The apparatus of claim 7, wherein each laser diode of each diode bar provides about 1 watt or more of power.

12. The apparatus of claim 11, wherein each 2D stack provides about 200 watts or more of power.

13. The apparatus of claim 7, the diode bars of each 2D stack have a same wavelength range as its corresponding 2D stack.

14. The apparatus of claim 7, wherein the laser diode arrays include deep UV (ultra-violet) and UV continuous wave diode lasers.

15. The apparatus of claim 7, wherein the laser diode arrays include VIS (visible) and NIR (near infrared) continuous wave diode lasers.

16. A method of generating a light source in a semiconductor inspection tool, comprising:
    selecting and activating one or more laser diode arrays to generate light at a selected inspection application's specified wavelength range while preventing other one or more laser diode arrays from generating light outside the specified wavelength range, wherein a first set of one or more of the 2D stacks is formed from deep UV or UV based laser diodes, a second set of one or more of the 2D stacks is formed from VIS based laser diodes, and a third set of one or more of the 2D stacks is formed from deep NIR based laser diodes;
    coupling light from the activated one or more laser diode arrays together to form an incident beam;
    directing the incident beam to a wafer or reticle;
    performing the selected inspection application based on light detected from the wafer or reticle in response to the incident beam; and
    repeating the operations for selecting and activating one or more laser diode arrays, coupling light, directing the incident beam, and performing the selected inspection application for a plurality of sequentially selected inspection applications having different specified wavelength ranges.

17. The method of claim 16, wherein the 2D stacks are formed from diode bars that can be selectively activated to result in the incident beam having different wavelength ranges that together form a broadband range.

18. The method of claim 16, wherein the 2D stacks are formed from diode bars.

19. The method of claim 16, wherein the diode bars that can be selectively activated to result in the incident beam having different wavelength ranges that together form a broadband range.

* * * * *